United States Patent [19]

Plant et al.

[11] 4,394,155
[45] Jul. 19, 1983

[54] SUBSTITUTED PYRIDINE 1-OXIDE HERBICIDES

[75] Inventors: Howard L. Plant, Milford; Steven E. Cantor; Arthur M. Doweyko, both of Cheshire, all of Conn.; Mark A. Dekeyser, Waterloo, Canada; Allyn R. Bell, Cheshire, Conn.

[73] Assignees: Uniroyal, Inc., New York, N.Y.; Uniroyal Ltd., Ontario, Canada

[21] Appl. No.: 231,813

[22] Filed: Feb. 5, 1981

[51] Int. Cl.$^3$ .................. A01N 43/40; C07D 213/64
[52] U.S. Cl. ........................................ 71/94; 546/294
[58] Field of Search ............................ 546/294; 71/94

[56] References Cited

U.S. PATENT DOCUMENTS

| | | | |
|---|---|---|---|
| 3,107,994 | 10/1963 | Rawlings et al. | 71/94 |
| 3,155,671 | 11/1964 | D'Amico | 71/94 |
| 3,960,542 | 6/1976 | Plant et al. | 546/270 |
| 4,019,893 | 4/1977 | Plant et al. | 71/94 |
| 4,026,937 | 5/1977 | Gulbenk | 71/94 |
| 4,120,692 | 10/1978 | Plant et al. | 546/301 |
| 4,201,567 | 5/1980 | Lee | 71/94 |
| 4,360,677 | 11/1982 | Doweyko et al. | 71/94 |

Primary Examiner—Ethel G. Love
Attorney, Agent, or Firm—James J. Long; Marvin Bressler

[57] ABSTRACT

Compounds of the following formula are effective as premergence herbicides:

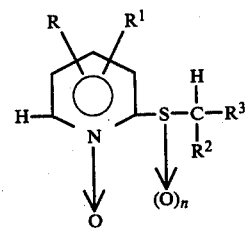

wherein R and $R^1$ may be the same or different and are $C_1$ to $C_4$ alkyl, $C_1$ to $C_4$ alkoxy, phenyl or halogen, provided that R or $R^1$ is not halogen if attached in the 3-position of the pyridine ring, and R or $R^1$ may further be hydrogen provided that one of them is one of the recited moieties other than hydrogen; $R^2$ is hydrogen, halogen, methyl or ethyl; $R^3$ is phenyl or phenyl substituted with halogen, $C_1$ to $C_4$ alkyl, $C_1$ to $C_4$ alkoxy, or nitro; and n is 1 or 2.

20 Claims, No Drawings

SUBSTITUTED PYRIDINE 1-OXIDE HERBICIDES

This invention relates to 2-sulfinyl or 2-sulfonyl 3-, 4- or 5-substituted pyridine 1-oxides and to herbicidal compositions containing such compounds, as well as to a method of controlling weeds using such compositions.

The compounds of the invention have the structural formula

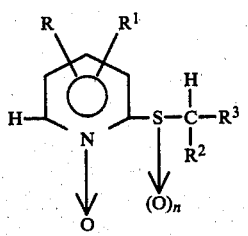

wherein R and $R^1$ may be the same or different and are $C_1$ to $C_4$ alkyl, $C_1$ to $C_4$ alkoxy, phenyl or halogen provided that R or $R^1$ is not halogen if attached in the 3-position of the pyridine ring, and R or $R^1$ may further be hydrogen provided that one of them is one of the recited moieties other than hydrogen; $R^2$ is hydrogen, halogen, methyl or ethyl, $R^3$ is phenyl or phenyl substituted with halogen, $C_1$ to $C_4$ alkyl, $C_1$ to $C_4$ alkoxy or nitro; and n is 1 or 2.

The compounds of the invention are particularly useful in the selective preemergence control of weeds, as evidenced especially in certain dicotyledonous crops.

U.S. Pat. No. 3,960,542, Plant et al, June 1, 1976, discloses herbicidal 2-sulfinyl and 2-sulfonyl pyridine 1-oxide derivatives of the formula:

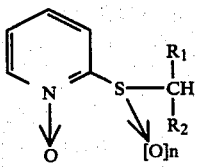

where n is 1 or 2; $R_1$ is hydrogen or methyl; $R_2$ may be mono or poly substituted phenyl.

U.S. Pat. No. 4,019,893, Plant et al, Apr. 26, 1977, teaches a method of controlling vegetation which comprises applying a phytotoxic concentration of one of the foregoing compounds.

W. Walter et al, Liebig's Ann., 695, 77 (1966), discloses 2-(phenylmethylsulfinyl)pyridine 1-oxide (also called 2-benzylsulfinylpyridine 1-oxide) and 2-(phenylmethylsulfonyl)pyridine 1-oxide (also called 2-benzylsulfonylpyridine 1-oxide), but no utility for these chemicals is disclosed.

U.S. Pat. No. 3,107,994, Rawlings et al, Oct. 22, 1963, discloses certain herbicidal 2-(alkenylthio)pyridine 1-oxides, while U.S. Pat. No. 3,155,671, D'Amico, Nov. 3, 1964, discloses certain herbicidal benzyl 2-thiopyridine 1-oxides.

U.S. Pat. No. 4,201,567, Lee, May 6, 1980 discloses certain 4- or 5-substituted pyridine 1-oxides, such as 2-[(1,1,2,2-tetrafluoroethyl)sulfinyl]pyridine 1-oxide, which exhibit selective preemergence control of weeds.

However, none of the above references indicate that the 3-, 4-, or 5-substituted pyridine 1-oxides of this invention would exhibit selective preemergence control of weeds. As indicated the compounds of the invention have the formula

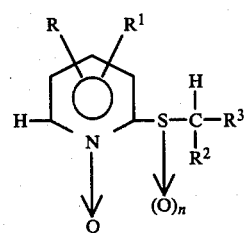

wherein R and $R^1$ may be the same or different and are $C_1$ to $C_4$ alkyl (e.g. methyl, ethyl, n-butyl, t-butyl) $C_1$ to $C_4$ alkoxy (e.g. methoxy, ethoxy, butoxy), phenyl or halogen (flourine, chlorine, bromine, iodine), provided that R or $R^1$ is not halogen if attached in the 3-position of the pyridine ring, and R or $R^1$ may further be hydrogen provided that one of them is one of the recited moieties other than hydrogen; $R^2$ is hydrogen, halogen (fluorine, chlorine, bromine or iodine) methyl or ethyl, $R^3$ is phenyl or phenyl substituted with halogen (fluorine, chlorine, bromine or iodine), $C_1$ to $C_4$ alkyl (e.g., methyl, ethyl, n-butyl, t-butyl), $C_1$ to $C_4$ alkoxy (e.g., methoxy, ethoxy, butoxy) or nitro, and n is 1 or 2.

Preferred compounds are those wherein R is hydrogen or $C_1$ to $C_4$ alkyl, $R^1$ is bromine, chlorine or $C_1$ to $C_4$ alkyl, and $R^3$ is phenyl or phenyl substituted with up to two groups selected from chlorine, methyl, methoxy and nitro.

The compounds of this invention are generally prepared by first preparing the appropriate thio compound. An essentially equimolar amount of an alkali metal alkoxide is added with stirring at room temperature under an atmosphere of nitrogen to the substituted or non-substituted benzylmercaptan, dissolved in a suitable solvent (such as a $C_1$ to $C_4$ aliphatic alcohol, preferably methanol). The resulting solution is added slowly to a solution of a substituted pyridine 1-oxide hydrochloride, which has been treated with an essentially equimolar amount of alkali metal alkoxide. The molar ratio of mercaptide anion to pyridine 1-oxide is maintained at about 1, and stirring, nitrogen atmosphere and reaction at room temperature are also maintained throughout the complete reaction. After all the reactants have been combined, the reaction mixture is refluxed from one to six hours. The thio product which precipitates when the reaction mixture is poured into a large excess of ice water is filtered, washed several times with water, air dried and recrystallized from an alcohol such as wet ethanol.

The thio compound is oxidized to the desired sulfinyl or sulfonyl compound by known means, e.g. the thio compound dissolved in excess chloroform is stirred into a chloroform solution of m-chloroperbenzoic acid at $-10°$ to $10°$ C. The reaction vessel is stoppered and kept at about $0°$ C. for about 24 hr. The by-product, m-chlorobenzoic acid, is removed by filtration and the remaining chloroform solution washed thoroughly with aqueous sodium bicarbonate solution, then water. The chloroform solution is dried (e.g. with anhydrous magnesium sulfate) and the solvent evaporated. The final product may be recrystallized from a suitable solvent (e.g. lower alcohol).

Weeds compete with crops for light, moisture, nutrients and space. Thus, weeds inhibit the production of foliage, fruit or seed of agricultural crops. The presence of weeds may also reduce the quality of the harvested crop and reduce harvesting efficiency. Weed control is essential for maximum production of many agronomic and horticultural crops including soybeans (*Glycine max* L.) peanuts (*Arachis hypogaea* L.) flax (*linum usitatissmium* L.) and cotton (*Gossypium* sp.).

The 3-, 4-, and 5-substituted pyridine 1-oxide derivatives of the invention are useful for preemergence control of weeds, and are furthermore remarkable for their ability to selectively control weeds without injury to desirable crops. Excellent control of weeds such as quackgrass [*Agropyron repens* (L.) Beauv.] from seed, Texas panicum (*Panicum texanum* Buckl.), giant foxtail (*Setaria faberi* Herrm.), yellow foxtail [*Setaria lutescens* (Weigel) Hubb.], green foxtail [*Setaria viridis* (L.) Beauv.], barnyardgrass [*Echinochloa crusgalli* (L.) Beauv.], and wild oats (*Avena fatua* L.) can be achieved without injury to such crops as flax (*Linum usitatissmium* L.), alfalfa (*Medicago sativa* L.), cotton (*Gossypium* sp.), soybeans [*Glycine max* (L.) Merr.], peanuts (*Arachis hypogaea* L.), tomatoes (*Lycopersicon esculentum* Mill.) and tobacco (*Nicotiana tabacum* L.).

The procedures for using the present 3-, 4- or 5-substituted pyridine 1-oxides as herbicides are in accordance with conventional agricultural practice. The chemicals are ordinarily applied as formulations containing a carrier and/or surface-active agent. The formulation may contain more than one of the described 3-, 4- or 5-substituted pyridine 1-oxide derivatives if desired; other active herbicides may be included in the formulation as well.

The chemical may be impregnated on finely divided or granular inorganic or organic carriers such as attapulgite clay, sand, vermiculite, corn cobs, activated carbon or other granular carriers known to the art. The impregnated granules may then be spread on the soil. Furthermore, the chemical may be formulated as a wettable powder by grinding it into a fine powder and mixing it with an inactive powdered carrier to which a surface active dispersing agent has been added. Typical powdered solid carriers are the various mineral silicates, e.g., mica, talc, pyrophyllite, and clays. The wettable powder may then be dispersed in water and sprayed on the soil surface or weeds. Similarly, an emulsifiable concentrate may be prepared by dissolving the chemical in a solvent such as benzene, toluene, or other aliphatic or aromatic hydrocarbon to which a surface active or dispersing agent has been added. The emulsifiable concentrate may then be dispersed in water and applied by spraying. Suitable surface active agents are well known to those skilled in the art, and reference may be had to McCutcheon's Detergents and Emulsifiers, 1970, Allured Publishing Corp.; or U.S. Pat. Nos. 2,614,916, Hoffman et al, Oct. 21, 1952, cols. 2 to 4 and 2,547,724, Sundholm, Apr. 3, 1951, cols. 3 and 4, for example of appropriate surface active agents. The concentration of active chemical in the formulation may vary widely, e.g., from 1 to 95%. The concentration of active chemical in dispersions applied to the soil is almost invariably from 0.002% to 75% by weight. The chemical is frequently applied at rates of 0.10 to 25 pounds per acre (0.112–28 kg/ha). For use as a preemergence herbicide, the chemical is applied to soil which contains weed and crop seed, either to the surface of the soil or incorporated into the upper one to three inches (2.54–7.6 cm) of soil.

The most suitable rate of application in any given case will depend on such factors as soil type, soil pH, soil organic matter content, the quantity and intensity of rainfall before and after treatment, the air and soil temperature, light intensity and light duration per day. All of these factors can have an influence on the efficacy of the chemicals for use as herbicides.

The herbicidal use may include selective weed control in crops such as soybeans, cotton, flax and peanuts.

Compounds of the invention may be used for selective control of various grasses and broadleaved weeds including pigweed (*Amaranthus retroflexus* L.) and purslane (*Portulaca oleracea* L.) in diverse crops including flax (*Linum usitatissimum* L.), alfalfa (*Medicago sativa* L.), cotton (*Gossypium* sp.), soybeans [*Glycine max* (L.) Merr.], peanuts (*Arachis hypogaea* L.), tomatoes (*Lycopersicon esculentum* Mill.) and tobacco (*Nicotiana tabacum* L.). Application may be in aqueous solutions or suspensions which may be sprayed onto the soil surface prior to weed and crop emergence and before or after the crop seed is sown. The soil may receive a shallow timing (less than 3 inches (7.6 cm)) after application of the chemical, but this is not required as it is with some preemergence herbicides. The compounds of this invention may also be applied by broadcast of a granular formulation prior to weed and crop emergence.

Compounds of this invention may be added as a "tank mix" to other herbicide solutions so that the number of different weed species controlled in a single application will be increased. The formulations of invention compounds may also include other herbicides so that the spectrum of weeds controlled by spray or granular application may be increased.

The following Example will serve to illustrate the practice of the invention in more detail.

EXAMPLE 1

2-[(2,5-Dimethylphenyl)methylsulfonyl]-5-methylpyridine 1-oxide:

Under a constant flow of nitrogen 3.0 g (0.02 mol) 2,5-dimethylbenzenemethanethiol dissolved in 50 mL of methanol is treated with 4.8 g (0.022 mol) 25% sodium methoxide in methanol. To this stirred mixture is added 4.4 g (0.022 mol) of 2-bromo-5-methylpyridine 1-oxide hydrochloride which has previously been treated with 4.8 g (0.022 mol) 25% sodium methoxide in methanol. The reaction mixture is allowed to reflux for 1.5 hours, cooled and poured into 250 mL ice-water. The product is filtered off and air dried to yield 4.6 g (88% of theory). Recrystallization from ethanol produces 2-[(2,5-dimethylphenyl)methylthio]-5-methylpyridine 1-oxide, mp 172°–174° C.

To a stirred solution of 3.0 g (0.011 mol) of the thio compound in 50 mL chloroform at 0°–10° C. is added 4.6 g (0.025 mol) of 85% pure m-chloroperoxybenzoic acid (MCPBA) dissolved in 200 mL chloroform. Upon completion of the addition, the temperature is permitted to reach ambient while stirring is continued for two days. The reaction mixture is washed thoroughly with 150 mL saturated sodium bicarbonate solution and water, then dried over anhydrous magnesium sulfate. Evaporation of the chloroform, and crystallization of the solid residue from ethanol yields 2.7 g (84% of theory) of product. Melting point 154°–156° C. (I.R. N→O 1275 cm$^{-1}$, SO$_2$ 1135, 1310 cm$^{-1}$).

| Elemental analysis: $C_{15}H_{17}NO_3S$ | | | | |
| --- | --- | --- | --- | --- |
| | C | H | N | S |
| Calculated: | 61.85 | 5.88 | 4.82 | 11.00 |
| Found: | 62.01 | 6.10 | 4.92 | 9.67 |

EXAMPLE 2

2-[(2,5-Dimethylphenyl)methylsulfonyl]-3-methylpyridine 1-oxide

To a stirred solution of 3.2 g of sodium in 30 mL absolute ethanol is added 10.6 g (2,5-dimethylbenzene)-methanethiol at room temperature. After stirring for one hour the reaction mixture is added slowly to a stirred suspension of 12 g 2-chloro-3-methylpyridine 1-oxide hydrochloride at room temperature. After the addition, the reaction mixture is heated at 50° C. for one hour then at room temperature overnight. Evaporation of the volatile material gives an oil. 200 mL of water are added and the mixture is extracted with 100 mL of chloroform three times. The chloroform solution is dried and evaporated to a solid. Recrystallization from toluene yields 8 g of sulfide. The melting point is 100°–103° C. This structure is confirmed by NMR, I.R. and elemental analysis.

To a stirred solution of 3.6 g (0.014 mol) of the sulfide in 2.5 mL methanol containing 0.15 g sodium tungstate is slowly added 3.5 mL of 30% hydrogen peroxide solution at room temperature. Stirring is continued for a few minutes, the reaction mixture then heated to 50° C. for 4 hours, and kept overnight at room temperature. Water is added to precipitate the product, which is filtered and then recrystallized from a mixture of toluene and ethanol. The melting point is 171°–173° C. The structure is confirmed by NMR, I.R.

| Elemental analysis: $C_{15}H_{17}NO_3S$ | | | | |
| --- | --- | --- | --- | --- |
| | C | H | N | S |
| Calculated: | 61.85 | 5.88 | 4.81 | 11.00 |
| Found: | 61.90 | 6.23 | 4.92 | 9.65 |

EXAMPLE 3

2-[(2,5-Dimethylphenyl)methylsulfinyl]-3-methylpyridine 1-oxide

The thio compound described in the previous example (0.03 mol) is oxidized with MCPBA (0.03 mol) in 100 mL chloroform. After 24 hours at room temperature the chloroform solution is treated as described in Example 1, yielding 5.5 g (66.6% yield) of a white solid m.p. 143°–145° C. from ethyl acetate. I.R. N→O 1230 cm$^{-1}$, S→O 1055 cm$^{-1}$.

| Elemental analysis: $C_{15}H_{17}NO_2S$ | | | | |
| --- | --- | --- | --- | --- |
| | C | H | N | S |
| Calculated: | 65.42 | 6.22 | 5.09 | 11.62 |
| Found: | 65.32 | 6.13 | 5.08 | 11.94 |

EXAMPLE 4

2-[1-(2,5-Dimethylphenyl)ethylsulfonyl]-3-methylpyridine 1-oxide

To a stirred suspension of 3 g (0.01 mol) of sulfone (described in Example 3) in 15 mL of dry dimethylformamide cooled in an ice bath, is added 0.5 g sodium hydroxide powder. To this mixture is slowly added 0.75 mL methyl iodide. The reaction mixture is warmed to room temperature and stirred for 2 hours. 100 mL ice-water is slowly added with stirring. After filtration the white solid is recrystallized from toluene. Melting point: 146°–147° C. Structure confirmed by NMR. I.R. N→O 1250 cm$^{-1}$, SO$_2$ 1350, 1140 cm$^{-1}$.

| Elemental analysis: $C_{15}H_{17}NO_3S$ | | | |
| --- | --- | --- | --- |
| | C | H | N |
| Calculated: | 61.85 | 5.88 | 4.81 |
| Found: | 61.95 | 5.65 | 5.26 |

EXAMPLE 5

2-(Phenylchloromethylsulfonyl)-5-chloropyridine 1-oxide

As described in Example 1, 2-(phenylmethylthio)-5-chloropyridine 1-oxide is prepared from 5-chloropyridine 1-oxide and benzylmercaptan. To a well stirred solution of 2.5 g (0.01 mol) of the thio compound in 25 mL chloroform is added 4 g (0.02 mol) of MCPBA in 50 mL chloroform.

The sulfone is dissolved in DMF (20 mL) containing 0.25 g powdered sodium hydroxide and 1.5 g carbon tetrachloride at 0° C. The mixture is maintained at 0° C. for 20 minutes then poured in 200 mL water. The solid was filtered and dried. The product (0.55 g) m.p. 178–179 (dec.) is identified by I.R., NMR and mass spectographic analysis.

| Elemental analysis: $C_{12}H_{11}NO_3ClS$ | | | |
| --- | --- | --- | --- |
| | C | H | N |
| Calculated: | 45.30 | 2.85 | 4.40 |
| Found: | 44.08 | 2.87 | 4.39 |

EXAMPLE 6

2-[1-(2,5-Dimethylphenyl)ethylsulfonyl]-5-methylpyridine 1-oxide

Under a constant flow of nitrogen 3.32 g (0.02 mol) 2-(ethyl-1-thiol)-1,4-dimethylbenzene dissolved in 75 mL methanol is treated with 4.8 g (0.022 mol) 25% sodium methoxide in 75 mL methanol. To this stirred mixture is added 4.4 g (0.02 mol) 2-bromo-5-methylpyridine 1-oxide hydrochloride which has previously been treated with 4.8 g (0.022 mol) sodium methoxide (25% in methanol). The reaction mixture is allowed to reflux for 1 hour, cooled and poured into 200 mL ice water. The white product is filtered off and air dried; yield 4.5 g (83%). Recrystallization from ethanol produces 2-[1-(2,5-dimethylphenyl)ethylthio]-5-methylpyridine 1-oxide, m.p. 146°–148° C. Structure is confirmed by analysis and I.R.

To a stirred solution of 2.85 g (0.01 mol) of the sulfide compound in 50 mL chloroform at 5°–10° C. is added, with stirring, 4.6 g (0.024 mol) MCPBA in 175 mL chloroform. Upon completion of the addition, the reaction mixture is stirred at room temperature for two days then washed thoroughly with 150 mL saturated aqueous sodium bicarbonate, and dried over anhydrous magnesium sulfate. Evaporation of the chloroform, and crystallization of the solid residue from ethanol yields 2.6 g (82% of theory) of product. m.p. 143°–146° C. (I.R. N→O 1280 cm$^{-1}$, SO$_2$ 1140, 1310 cm$^{-1}$).

| Elemental analysis: $C_{16}H_{19}NO_3S$ | | | |
| --- | --- | --- | --- |
| | C | H | N | S |
| Calculated: | 62.92 | 6.27 | 4.58 | 10.50 |
| Found: | 62.56 | 6.09 | 4.52 | 10.25 |

EXAMPLE 7

2-[1-(2,5-Dimethylphenyl)ethylsulfonyl]-4-methylpyridine 1-oxide

The intermediate 2-[1-(2,5-dimethylphenyl)ethylthio]-4-methylpyridine 1-oxide is prepared from 2-(ethyl-1-thiol)-1,4-dimethylbenzene and 2-bromo-4-methylpyridine 1-oxide hydrochloride by the procedure described in Example 1. m.p. 130°–132° C. Structure is confirmed by analysis and I.R. Yield 98%.

The thio compound (0.07 mol) is oxidized in the manner described in Example 1. Yield 79%. Melting point 204°–205° C. (I.R. N→O 1240 cm$^{-1}$, SO$_2$ 1140, 1370 cm$^{-1}$.)

| Elemental analysis: $C_{16}H_{19}NO_3S$ | | | |
| --- | --- | --- | --- |
| | C | H | N | S |
| Calculated: | 62.92 | 6.27 | 4.58 | 10.50 |
| Found: | 61.79 | 6.20 | 4.51 | 10.19 |

EXAMPLE 8

2-[(2,5-Dimethylphenyl)methylsulfonyl]-4-methylpyridine 1-oxide

The intermediate 2-[1-(2,5-dimethylphenyl)ethylthio]-4-methylpyridine 1-oxide is prepared from 2,5-dimethylbenzenemethanethiol and 2-bromo-4-methylpyridine 1-oxide hydrochloride by the procedure described in Example 1. m.p. 130°–132° C. Structure is confirmed by analysis and I.R.

The sulfide compound (0.006 mole) is oxidized with MCPBA (0.014 mol) and is isolated in the manner described in Example 1. Yield 62% of theory. Melting point 156°–158° C. from ethanol/water (80/20 v/v) I.R. N→O 1275 cm$^{-1}$, SO$_2$ 1135, 1310 cm$^{-1}$.

| Elemental analysis: $C_{15}H_{17}NO_3S$ | | | |
| --- | --- | --- | --- |
| | C | H | N | S |
| Calculated: | 61.85 | 5.88 | 4.81 | 11.00 |
| Found: | 60.72 | 5.38 | 4.92 | 10.67 |

EXAMPLE 9

2-[(2,5-Dimethylphenyl)methylsulfonyl]-4,5-dimethylpyridine 1-oxide 2,3-Dimethylbutadiene (3.2 g, 0.04 mol) and 1.0 g (0.0048 mol) of (2,5-dimethylbenzene)methanesulfonylcyanide are allowed to reflux for 2 hours. The mixture is evaporated under reduced pressure and the residue extracted with n-hexane to remove unreacted sulfonylcyanide. The residue crystallizes upon standing at room temperature to yield 0.30 g 2-[(2,5-dimethylphenyl)methylsulfonyl]-4,5-dimethylpyridine.

The above compound is dissolved in 25 mL chloroform and treated with 1.7 g MCPBA (0.01 mol) for several days at room temperature. The mixture is washed with aqueous sodium carbonate, filtered and dried. The chloroform solution is concentrated under reduced pressure resulting in 0.20 g solid product. Recrystallization from methanol produces white crystals (0.13 g) of the title compound; m.p. 188–91° C. The structure is confirmed by I.R., NMR and mass spectrographic analysis.

EXAMPLE 10

3-Methyl-2-[1-(2-methyl-3-nitrophenyl)ethylsulfonyl]-pyridine 1-oxide

A mixture of 10 g (0.06 mol) 2-chloro-3-methylpyridine 1-oxide, 2.8 g (0.07 mol) sodium hydroxide powder, and 8 g (0.06 mole) sodium sulfide is stirred in 40 mL water and heated to 70° C. for 2½ hours. After cooling in ice-water, 11 g (0.06 mol) of 2-methyl-3-nitrobenzyl chloride and 20 mL methanol are added dropwise and the resulting mixture heated to 70° C. for 2 hours. After standing at room temperature overnight, the precipitate is filtered and recrystallized from toluene. Melting point: 115°–117° C. Structure is confirmed by NMR.

To a stirred suspension of 5.5 g (0.02 mol) of the sulfide and 30 mL glacial acetic acid is added 7.6 g (0.04 mol) of 40% peracetic acid solution. The mixture is heated to 50° C. for 5 hours, cooled and then neutralized with an aqueous solution of potassium carbonate. The precipitate is filtered. Melting point: 187°–191° (dec.) Structure is confirmed by I.R., NMR and elemental analysis.

To a stirred suspension of 3.2 g (0.01 mol) of sulfone in 20 mL dimethylformamide is added 0.5 g (0.01 mol) of sodium hydroxide powder followed by the slow addition of 0.6 mL (0.01 mole) methyl iodide. The methyl mixture is stirred at room temperature for one hour, then diluted with water and let stand overnight. The precipitate is filtered. Melting point: 208°–211° C. Structure is confirmed by NMR and elemental analysis.

| Elemental analysis: $C_{15}H_{16}N_2O_5S$ | | |
| --- | --- | --- |
| | C | H | N |
| Calculated: | 53.57 | 4.80 | 8.33 |
| Found: | 53.46 | 4.86 | 8.69 |

In accordance with the same procedure the chemicals listed in TABLE I may be prepared. In TABLE I, X in the column headed I.R. indicates that the structure is confirmed by infrared spectrum examination and X in the column headed NMR indicates that the structure is confirmed by nuclear magnetic resonance observation.

TABLE I

2-SULFINYL & 2-SULFONYL SUBSTITUTED PYRIDINE-1-OXIDES

| Example | NAME | m.p. °C. | C | H | N | S | Cl | I.R. | NMR |
| --- | --- | --- | --- | --- | --- | --- | --- | --- | --- |
| 11 | 4-methyl-2-[phenylmethylsulfonyl]-pyridine 1-oxide | 142–144 | 59.29 / 59.29 | 4.97 / 4.78 | 5.32 / 5.24 | 13.50 / 12.70 | | X | |

TABLE I-continued

2-SULFINYL & 2-SULFONYL SUBSTITUTED PYRIDINE-1-OXIDES

| Example | NAME | m.p. °C. | C | H | N | S | Cl | I.R. | NMR |
|---|---|---|---|---|---|---|---|---|---|
| 12 | 2-[(2,4-dimethylphenyl)methylsulfonyl]-3-methylpyridine 1-oxide | 153–158 | 61.85 / 61.63 | 5.88 / 5.76 | 4.81 / 4.99 | | | | X |
| 13 | 2-[1-(2,4-dimethylphenyl)ethylsulfonyl]-3-methylpyridine 1-oxide | 172–174 | 62.94 / 62.77 | 6.27 / 6.43 | 4.59 / 4.58 | | | X | X |
| 14 | 2-[(2-chlorophenyl)methylsulfonyl]-3-methylpyridine 1-oxide | 162–167 | 52.43 / 52.25 | 4.06 / 3.90 | 4.70 / 4.28 | | | X | X |
| 15 | 2-[1-(2-chlorophenyl)ethylsulfonyl]-3-methylpyridine 1-oxide | 178–182 | 53.92 / 53.95 | 4.52 / 4.55 | 4.49 / 4.56 | | | X | X |
| 16 | 3-methyl-2-[(2-methyl-3-nitrophenyl)methylsulfonyl]pyridine 1-oxide | 187–191 (dec) | 52.17 / 52.31 | 4.38 / 4.39 | 8.69 / 8.86 | | | X | X |
| 17 | 5-chloro-2-(phenylmethylsulfonyl)pyridine 1-oxide | 118–121 | 50.80 / 50.38 | 3.55 / 3.47 | 4.94 / 4.99 | | | X | X |
| 18 | 5-chloro-2-[(2,5-dimethylphenyl)methylsulfinyl]pyridine 1-oxide | 150–153 | 56.85 / 57.03 | 4.77 / 4.74 | 4.74 / 4.81 | | | X | X |
| 19 | 2-[(2,5-dimethylphenyl)chloromethylsulfonyl]-4-methylpyridine 1-oxide | 191(dec) | 55.30 / 55.39 | 4.95 / 5.09 | 4.30 / 4.39 | | | | |
| 20 | 2-[(2,5-dimethylphenyl)chloromethylsulfonyl]-5-methylpyridine 1-oxide | 128(dec) | | | | | | X | X |
| 21 | 3-methyl-2-(phenylmethylsulfonyl)pyridine 1-oxide | 186–190 (dec.) | 59.34 / 59.31 | 5.02 / 4.98 | 5.55 / 5.32 | | | X | X |
| 22 | 3-methyl-2-(1-phenylethylsulfonyl)pyridine 1-oxide | 146–149 | 60.64 / 60.66 | 5.45 / 5.32 | 5.05 / 4.90 | | | X | X |
| 23 | 3-methyl-2-[1-(2-methylphenyl)ethylsulfonyl]pyridine 1-oxide | 165–170 | 61.85 / 61.81 | 5.88 / 6.07 | 4.81 / 5.68 | | | X | X |
| 24 | 3-methyl-2-[(2-methylphenyl)methylsulfonyl]pyridine 1-oxide | 179–183 | 60.64 / 60.61 | 5.45 / 5.51 | 5.05 / 5.20 | | | X | X |
| 25 | 5-chloro-2-[(2,5-dimethylphenyl)methylsulfonyl]pyridine 1-oxide | 161–164 | 53.93 / 53.76 | 4.53 / 4.34 | 4.49 / 4.47 | | | X | |
| 26 | 2-[(4-chlorophenyl)methylsulfinyl]-4-methylpyridine 1-oxide | 160–163 | 55.41 / 53.51 | 4.29 / 4.32 | 4.96 / 4.85 | 11.37 / 10.87 | 12.58 / 12.49 | | |
| 27 | 2-[(4-chlorophenyl)methylsulfonyl]-4-methylpyridine 1-oxide | 180–182 | 52.44 / 52.06 | 4.06 / 4.06 | 4.70 / 4.57 | 10.76 / 10.58 | 11.90 / 11.99 | X | |

TABLE I-continued

2-SULFINYL & 2-SULFONYL SUBSTITUTED PYRIDINE-1-OXIDES

| Example | NAME | m.p. °C. | C | H | N | S | Cl | I.R. | NMR |
|---|---|---|---|---|---|---|---|---|---|
| 28 | 2-[1-(2,5-dimethyl-phenyl)propylsul-fonyl]-3-methyl-pyridine 1-oxide | 124–129 | 63.93<br>63.85 | 6.63<br>6.52 | 4.39<br>4.32 | | | X | X |
| 29 | 4-methyl-2-(phenyl-methylsulfinyl)pyridine 1-oxide | 131–133 | 63.14<br>63.10 | 5.29<br>5.25 | 5.69<br>5.58 | 12.96<br>12.79 | | | |

EXAMPLE 30

2-[(4-Methoxyphenyl)methylsulfonyl)]-4-(1,1-dimethylethyl)pyridine 1-oxide

Under nitrogen blanket 0.02 mol 4-methoxybenzylmercaptan is dissolved in 50 mL methanol and is treated with 0.022 mol sodium methoxide (25% in methanol). 2-Bromo-4-t-butylpyridine 1-oxide hydrochloride (0.022 mol, previously treated with 0.22 mol sodium methoxide (25% in methanol)) is added with stirring. After ca. 1.5 hours at reflux, the reaction mixture is cooled and poured into 250 mL ice water. After filtration, the product, 2-[(4-methoxyphenylmethylthio]-4-(1,1-dimethylethyl)pyridine 1-oxide, is recrystallized from ethanol. This product is converted to the corresponding sulfonyl compound following essentially the procedure of Example 3.

The resultant product is tested according to the procedure of Example 32 with similar herbicidal results.

EXAMPLE 31

2-[2,5-Dimethylphenyl)methylsulfonyl]-4-phenylpyridine 1-oxide (2,5-Dimethylbenzene methanethiol (0.2 mol) is reacted with 2-bromo-4-phenylpyridine 1-oxide hydrochloride (0.022 mol) following the outline of Example 1. The resultant thio compound is oxidized to the above named sulfonyl compound using the procedure of Example 3.

When applying this chemical to weeds as described in Example 32, similar herbicidal results are achieved.

EXAMPLE 32

To illustrate effectiveness of the described 3-, 4- and 5-substituted pyridine 1-oxides as preemergent herbicides, 600 mg chemical is dissolved in 10 mL organic solvent (e.g., acetone) to which 30 mg conventional emulsifying agent (e.g., isooctyl polyethoxyethanol, "Triton X100" [trademark]) is added. The solution is diluted to 100 mL with distilled water. Twenty milliliters of this 6000 ppm solution is diluted to 250 ppm with distilled water. The chemical is applied at the rate of 10 lbs/a (pounds per acre) (11.2 kg/ha) by drenching 46 mL of the 250 ppm solution on the surface of soil in 4½ inch (11.43 cm) diameter plastic pots which had been sown with the following weed seeds: rough pigweed (*Amaranthus retroflexus* L.) jimsonweed (*Datura stramonium* L.), tall morning-glory *Ipomea purpurea* (L.) Roth), switchgrass (*Panicum virgatum* L.), or crabgrass [*Digitaria ischaemum* (Schreb.) Muhl.], barnyardgrass (*Echinochloa crusgalli* (L.) Beauv.) and green foxtail [*Setaria viridis* (L.) Beauv.], or giant foxtail (*Setaria faberi* Herrm.). The percent control of the weeds compared to untreated checks is determined two weeks after treatment. Table II shows the results with the preemergence herbicides of the invention prepared in accordance with the above examples.

TABLE II

HERBICIDE ACTIVITY AT 10 POUNDS PER ACRE
(11.2 kg per ha)
PERCENT WEED CONTROL

| Ex. | Pigweed | Jimson Weed | Morning glory | Barnyard Grass | Switch grass | Green Foxtail |
|---|---|---|---|---|---|---|
| 18 | 100 | 50 | 100 | 100 | 100* | 100** |
| 25 | 100 | 0 | 0 | 100 | 100* | 100** |
| 17 | 100 | 0 | 0 | 98 | 100* | 100** |
| 9 | 20 | 50 | 20 | 95 | 100 | 100 |
| 7 | 100 | 0 | 75 | 95 | 100 | 98 |
| 3 | 100 | 0 | 25 | 98 | 100 | 98 |
| 2 | 80 | 0 | 0 | 95 | 100 | 95 |
| 4 | 100 | 0 | 50 | 98 | 100 | 100 |
| 1 | 95 | 0 | 0 | 95 | 100 | 95 |
| 6 | 25 | 0 | 0 | 98 | 100 | 98 |
| 8 | 95 | 0 | 0 | 98 | 100 | 95 |
| 5 | 90 | 0 | 0 | 75 | 98 | 90 |
| 19 | — | 0 | 0 | 50 | 100 | 100 |
| 13 | 0 | 0 | 0 | 98 | 100 | 100 |
| 28 | — | 0 | 0 | 40 | 100 | 100 |
| 22 | — | 0 | 0 | 98 | 100 | 100 |
| 29 | 100 | 0 | 0 | 100 | 100 | 100 |
| 20 | 0 | 0 | 0 | 25 | 0 | 25 |
| 24 | — | 0 | 0 | 98 | 98 | 95 |
| 23 | — | 0 | 0 | 98 | 100 | 98 |
| 15 | 0 | 0 | 0 | 90 | 90 | 40 |
| 12 | 0 | 0 | 0 | 50 | 30 | 30 |
| 14 | — | 0 | 0 | 70 | 20 | 75 |
| 16 | 0 | 0 | 0 | 80 | 0 | 20 |
| 10 | — | 0 | 0 | 80 | 60 | 30 |
| 26 | — | 0 | 0 | 100 | 100 | 100 |
| 27 | — | 0 | 0 | 90 | 100 | 95 |
| 21 | — | 0 | 0 | 40 | 0 | 100 |
| 11 | 0 | 0 | 0 | 98 | 98 | 95 |

*Crabgrass was substituted for switchgrass in this test.
**Giant foxtail was substituted for green foxtail in this test.

EXAMPLE 33

Selectivity of a herbicide is desirable since it allows control of weeds growing among desirable crop plants. To illustrate the usefulness of the compounds of this invention as selective preemergence herbicides, 0.4 g chemical is dissolved in 5.0 ml organic solvent such as acetone containing 25 mg conventional emulsifying agent (e.g., isoctyl polyethoxyethanol), diluted to 50 ml with distilled water and sprayed at the rate of 2 lb. (0.91 kg) active compound in 30 gallons (114 L) water per acre (ca. 0.4 ha) onto the surface of soil contained in 15×20 inch (38×51 cm) flats. Weed and crop seeds were sown in the soil prior to treatment. The percent weed control and crop injury were evaluated two weeks after treatment. TABLE III illustrates the usefulness of these chemicals as selective preemergence herbicides.

TABLE III

Selective Preemergence Herbicide Test

| | | Percent Crop Injury | | | |
|---|---|---|---|---|---|
| Ex. | Cucumber | Pinto Beans | Cotton | Soybeans | Sugar Beet |
| 25 | 35 | 0 | 0 | 20 | 0 |
| 7 | 20 | 0 | 0 | 40 | 30 |
| 4 | 30 | 20 | 20 | 75 | 30 |
| 6 | 20 | 20 | 20 | 35 | 0 |

| | | Percent Weed Control | | | |
|---|---|---|---|---|---|
| Ex. | Pigweed | Goose Grass | Wild Oats | Switch Grass | Green Foxtail | Barnyard Grass |
| 25 | 90 | 100 | 95 | 100 | 95 | 100 |
| 7 | 100 | 100 | 100 | 100 | 100 | 100 |
| 4 | 100 | 100 | 90 | 100 | 100 | 100 |
| 6 | 50 | 85 | 50 | 85 | 95 | 80 |

EXAMPLE 34

Listed below are non-limiting examples of formulations which can be used in this invention.

1. 9.6% Active Emulsifiable Concentrate
   a. 2-[1-(2,5-Dimethylphenyl)ethylsulfonyl]-4-methylpyridine 1-oxide — 0.6 g
   b. Blend of oil soluble sulfonates with polyoxyethylene ethers (Emcol [trademark] N39-BU e.g., nonylphenol polyoxyethylene plus calcium dodecylbenzene sulfonate) — 0.55 g
   c. Chloroform — 2.4 g
   d. Benzaldehyde — 2.7 g
2. 11.3% Active Soluble Concentrate
   a. 2-[1-(2,5-Dimethylphenyl)ethylsulfonyl]-4-methylpyridine 1-oxide. — 24.0 g
   b. Blend of oil soluble sulfonates with polyoxyethylene ethers (Emcol N5003 e.g., sodium lignin sulfonate plus polycondensate of ethylene oxide, propylene oxide and propylene glycol) — 12.0 g
   c. Phenol (90% aqueous solution) — 175.5 g
3. 50% Active Wettable Powder
   a. 2-[1-(2,5 Dimethylphenyl)ethylsulfonyl]-4-methylpyridine 1-oxide — 300 g
   b. Alkylaryl polyether alcohol OPE (octylphenoxypolyethoxyethanol) 9-10 units (Triton [trademark] X-120) — 6 g
   c. Sodium N—methyl-N—palmitoyl taurate (Igepon [trademark] TN-74) — 6 g
   d. Polymerized sodium salts of alkylnapthalene sulfonic acid (Daxad [trademark] 11) — 12 g
   e. Kaolinite clay (Dixie Clay [trademark]) — 84 g
   f. Hydrated amorphous silica (Hi Sil [trademark] 233) — 192 g
4. 5% Active Granule
   a. 2-[1-(2,5 Dimethylphenyl)ethylsulfonyl]-4-methylpyridine 1-oxide — 1.0 g
   b. Methylene chloride — 9.0 g
   c. Above solution sprayed onto hydrated magnesium aluminum Silicate 25/50 mesh (Attaclay [trademark]) — 19.0 g

What is claimed is:

1. A compound having the structural formula

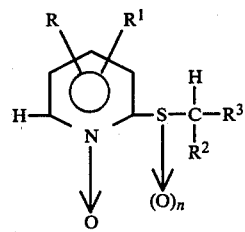

wherein R and $R^1$ may be the same or different and are $C_1$ to $C_4$ alkyl, $C_1$ to $C_4$ alkoxy, phenyl or halogen provided that R or $R^1$ is not halogen if attached in the 3-position of the pyridine ring, and R or $R^1$ may further be hydrogen provided that one of them is one of the recited moieties other than hydrogen; $R^2$ is hydrogen, halogen, methyl or ethyl; $R^3$ is phenyl or phenyl substituted with halogen, $C_1$ to $C_4$ alkyl, $C_1$ to $C_4$ alkoxy, or nitro; and n is 1 or 2.

2. A compound as in claim 1 wherein R is hydrogen or $C_1$ to $C_4$ alkyl; $R^1$ is bromine, chlorine or $C_1$ to $C_4$ alkyl; and $R^3$ is phenyl or phenyl substituted with up to two groups selected from chlorine, methyl, methoxy and nitro.

3. The compound of claim 1 which is 2-[(2,5-dimethylphenyl)methylsulfonyl]-5-methylpyridine 1-oxide.

4. The compound of claim 1 which is 2-[(2,5-dimethylphenyl)methylsulfonyl]-3-methylpyridine 1-oxide.

5. The compound of claim 1 which is 2-[(2,5-dimethylphenyl)methylsulfonyl]-3-methylpyridine 1-oxide.

6. The compound of claim 1 which is 2-[1-(2,5-dimethylphenyl)ethylsulfonyl]-3-methylpyridine 1-oxide.

7. The compound of claim 1 which is 5-chloro-2-(phenylchloromethylsulfonyl)pyridine 1-oxide.

8. The compound of claim 1 which is 2-[1-(2,5-dimethylphenyl)ethylsulfonyl]-5-methylpyridine 1-oxide.

9. The compound of claim 1 which is 2-[1-(2,5-dimethylphenyl)ethylsulfonyl]-4-methylpyridine 1-oxide.

10. The compound of claim 1 which is 2-[(2,5-dimethylphenyl)methylsulfonyl]-4-methylpyridine 1-oxide.

11. The compound of claim 1 which is 2-[(2,5-dimethylphenyl)methylsulfonyl]-4,5-dimethylpyridine 1-oxide.

12. The compound of claim 1 which is 3-methyl-2-[1-(2-methyl-3-nitrophenyl)ethylsulfonyl]pyridine 1-oxide.

13. The compound of claim 1 which is 5-chloro-2-(phenylmethylsulfonyl)pyridine 1-oxide.

14. The compound of claim 1 which is 5-chloro-2-[(2,5-dimethylphenyl)methylsulfinyl]pyridine 1-oxide.

15. The compound of claim 1 which is 5-chloro-2-[(2,5-dimethylphenyl)methylsulfonyl]pyridine 1-oxide.

16. The compound of claim 1 which is 4-methyl-2-(phenylmethylsulfinyl)pyridine 1-oxide.

17. The compound of claim 1 which is 3-methyl-2-[1-(2-methylphenyl)ethylsulfonyl]pyridine 1-oxide.

18. The compound of claim 1 which is 3-methyl-2-[(2-methylphenyl)methylsulfonyl]pyridine 1-oxide.

19. A herbicidal composition comprising a compound of any of claims 1 to 18 in a herbicidally effective amount in admixture with a carrier therefor.

20. A herbicidal method comprising applying, to a locus at which it is desired to control weeds, a herbicidally effective amount of a compound as in any of claims 1 to 18.

* * * * *